US007355009B2

(12) United States Patent
Jegla et al.

(10) Patent No.: US 7,355,009 B2
(45) Date of Patent: Apr. 8, 2008

(54) ANTIBODIES TO HUMAN ELK, A VOLTAGE-GATED POTASSIUM CHANNEL SUBUNIT

(75) Inventors: Timothy J. Jegla, Durham, NC (US); Alan Wickenden, Cary, NC (US)

(73) Assignee: Icagen, Inc., Durham, NC (US)

( * ) Notice: Subject to any disclaimer, the term of this patent is extended or adjusted under 35 U.S.C. 154(b) by 314 days.

(21) Appl. No.: 10/966,297

(22) Filed: Oct. 15, 2004

(65) Prior Publication Data

US 2005/0227250 A1    Oct. 13, 2005

Related U.S. Application Data

(62) Division of application No. 10/160,224, filed on May 28, 2002, now Pat. No. 6,833,440, which is a division of application No. 09/343,494, filed on Jun. 30, 1999, now Pat. No. 6,413,741.

(60) Provisional application No. 60/091,469, filed on Jul. 1, 1998, provisional application No. 60/116,621, filed on Jan. 21, 1999.

(51) Int. Cl.
*C07K 16/28* (2006.01)
(52) U.S. Cl. ............... 530/387.1; 530/388.1; 530/388.2; 530/389.1
(58) Field of Classification Search ............ None
See application file for complete search history.

(56) References Cited

FOREIGN PATENT DOCUMENTS

| WO | WO 99/37677 | 7/1999 |
|---|---|---|
| WO | WO 00/03687 A2 | 1/2000 |
| WO | WO 00/05346 | 2/2000 |
| WO | WO 00/22001 A2 | 4/2000 |

OTHER PUBLICATIONS

Bowie, James U. et al.; "Deciphering the message in protein sequences: tolerance to amino acid substitutions"; *Science*; Mar. 16, 1990; pp. 1306-1310; vol. 247, No. 4948.
Brüggemann, A. et al., "Ether-à-go-go encodes a voltage-gated channel permeable to $K^+$ and $Ca^{2+}$ and modulated by cAMP," *Nature*, 365:445-447 (1993).
Frings, S. et al., "Characterization of Ether-à-go-go Channels Present in Photoreceptors Reveals Similarity to $l_{Kx}$, a $K^+$ Current in Rod Inner Segments," *J. Gen. Physiol.*, 111:583-599 (1998).
Kerlavage et al., GenBank Accession No. AA 325048.1, Apr. 20, 1997.
London, B., et al., "Two Isoforms of the Mouse *Ether-a-go-go*-Related Gene Coassemble to Form Channels With Properties Similar to the Rapidly Activating Component of the Cardiac Delayed Rectifier K+ Current," *Circulation Research*, 81(5):870-878 (1997).
Ludwig, J. et al., "Functional expression of a rat homologue of the voltage gated *ether à go-go* potassium channel revelas differences in selectivity and activation kinetics between the *Drosophila* channel and its mammalian counterpart," *EMBO Journal*, 13(19):4451-4458 (1994).
Mickle, John and Garry R. Cutting; "Genotype-phenotype relationships in cystic fibrosis"; *Inherited Diseases of the Pancreas*; May 2000; pp. 597-607; vol. 84, No. 3; Medical Clinics of North America.
Mikayama, T.; "Molecular cloning and functional expression of cDNA encoding glycosylation-inhibiting factor"; *Proc. Natl. Acad. Sci. USA.*; 1993, pp. 10056-10060; vol. 90.
Occhiodoro, T. et al., "Cloning of a human *ether-a-go-go* potassium channel expressed in myoblasts at the onset of fusion," *FEBS Letters*, 434:177-182 (1998).
Robertson, G.A. et al., "Potassium Currents Expressed from *Drosophila* and Mouse *eag* cDNAs in *Xenopus* Oocytes," *Neuropharmacology*, 35(7):841-850 (1996).
Sanguinette, M.C. and P.S. Spector; "Potassium Channelopathies"; *Neuropharmacology*; 1997, pp. 755-762; vol. 36, No. 6; Pergamon.
Sara Volorio et al., "Sequencing analysis of Forty-Eight Human Image cDNA Clones Similar to *Drosophila* Mutant Protein," May 8, 1998, DNA Sequence—The Journal of Sequencing and Mapping, vol. 9 (5-6), pp. 307-315.
Shi, W. et al., "Cloning of a mammalian *elk* potassium channel gene and EAG mRNA distribution in rat sympathetic ganglia," *J. of Physiol.*, 511.3:675-682 (1998).
Shi, W. et al., "Identification of Two Nervous System-Specific Members of the *erg* Potassium Channel Gene Family," *J. of Neuroscience*, 17(24):9423-9432 (1997).
Voet et al.; *Biochemistry*; 1990, pp. 126-128 and 228-234; John Wiley & Sons, Inc.
Warmke, J. et al., "A Distinct Potassium Channel Polypeptide Encoded by the *Drosophila eag* Locus," *Science*, 252:1560-1562 (1991).
Warmke, J.W. and Barry Ganetzky, "A family of potassium channel genes related to *eag* in *Drosophila* and mammals," *Proc. Natl. Acad. Sci. USA*, 91:3438-3442 (1994).
Wilson et al., GenBank Accession No. AA 772836, Jan. 29, 1998.
Zollo et al., GenBank Accession No. U69184, Apr. 23, 1998.
Zollo, M. et al., "Human DRES sequences," Database EST, Telethon Institute of Genetics and Medicine (Milan, Italy) No. U69184 (Apr. 1998).

*Primary Examiner*—Marianne P Allen
(74) *Attorney, Agent, or Firm*—Townsend and Townsend and Crew LLP

(57) ABSTRACT

The invention provides isolated nucleic acid and amino acid sequences of hElk, antibodies to hElk, methods of detecting hElk, methods of screening for voltage-gated potassium channel activators and inhibitors using biologically active hElk, and kits for screening for activators and inhibitors of voltage-gated potassium channels comprising hElk.

3 Claims, 6 Drawing Sheets

```
  1 MPAMRGLLAPQNTFLDTIATRFDGTHSNFVLGNAQVAGLFFVYCSDGFCDLTGFSRAEV  hElk2.PRO
  1 MPARKGLLAPQNTFLDTIATRFDGTHSNFVLGNAQANGN-EIVYCSDGFVDLTGYSRAQI  dElk.PRO

61 MQRGQASFLYGPDTISELVRQQIRKADEHKEFKAELIIIYRKSGIPFWCLIDVIPIKNEK  hElk2.PRO
 61 MQKGQSHFLYGPDIKEEHKQQJEKSISNKMELKIEVIFYKKEGAPFWCIFDIVPIKNEK  dElk.PRO

121 GEVALFIVSHKDISETK--------------------------------------NRG  hElk2.PRO
121 RDVVLFIASHKDITHIKMLEMNVNEECDSVFALTAALLGARFRAGSNAGMLGLGLPGLG  dElk.PRO

141 GPDRWKETGGRRRYGRARSKGEANRRRSRAVLYHISGHLQKQPKG---KHKINKG---VF  hElk2.PRO
180 GPAASDGDTEAGEGNNLDVPAGONMGRRRSRAVLYQLSGHYKPEKGGVKTIKIKIGNNFMH  dElk.PRO

197 GEKPNIPEYKIVAAIRKSPFIIIHCGALRATWDGFIIIATLYVAVIVPYSVCVSTAREPSA  hElk2.PRO
240 STEAPFPEYKTQSIKKSRLIIPHYVFKGIMDWIIVATFYVALMVPYNAAFAKADRQT-  dElk.PRO

257 ARFPPSVCDLAVEVFIIDIVLNFRTTFVSKSGQVFAPKSICLHYVTTWFLLDVIAAALP  hElk2.PRO
299 -----KVSDVIVEALFIVDILLNFRTTFVSRKGEVVSNSKQHAINYLRGWFALDLIAALP  dElk.PRO

317 FDIIHAFKVNVYFGA-----HILKTVRLLRILRLIPRLDRYSQYSAVVTLLMAVFAHAH  hElk2.PRO
354 FDHII--YASDIYDGEDSHIEIVKLTRLLRIARLIQKIDRYSQHTAMILTLLMFSFIIAAH  dElk.PRO

373 WVACVWFYQGQREIESSESELPEIGWLQELARRLETPYYLVGRRPAGGNSSGQSDNCSSS  hElk2.PRO
412 WIACIWYVAVKEYEWFPE---SNIGWLQLLAER----------------------  dElk.PRO

433 SEANGTGLEIIGGPSLRSAYIISLYFALSSLTSVGFGNVSANTDTEKIFSICTMLIGALM  hElk2.PRO
443 ---KNASVAILTTAE---TYSIIALYEFTISLTSVGFGNVSANTAEKVETIIMMLIGALM  dElk.PRO
```

FIG. 1A.

```
493  HAVVFGNVTAIIQRMYARRFLYHSRTRDLRDYIRIHRIPKPLKQRMLEYFQATWAVNNGI  hElk2.PRO
497  HAVVFGNVTAIIQRMYSRRSLYESKWRDIKDFVAIHNMPKELKQRIEDYFQTSWSLSHGI  dElk.PRO

553  DTTELQSIPDELRADIAMHLHKEVLQLPIFEAASRGCIRASIALRPAFCTPGEYLIHQ-   hElk2.PRO
557  DIYETIREFPELRGDVSMHLHREILQLPIFEAASQGCIKLSIHKTNFCAPGEYLIHK-   dElk.PRO

613  GDALQAIYFVQSGSMEVIKGGTVIAILGKGDLIGCELPRR-----------------EQ  hElk2.PRO
617  GDALNYIYIQNGSMEVIKDDMVVAILGKGDIVGSDINVHLVATSNGQMTATTNSAGQDV  dElk.PRO

655  VVKANADVKGLTYCVIQCLQLAGIHDSTALYPEFAPRFSRGLRGESYNLGAGGGSAEVD  hElk2.PRO
677  VVRSSDIKALTYCDELKCIHMGIVEVLRLYPEYQQQFANDIQHDLTCNLREGYENQDSD  dElk.PRO

715  TS-------SLSGDNTLMSTLEE------KETDGEQGPTVSP------APADEPSSPLLISPG  hElk2.PRO
737  IGPSFPLPSISEDDENREEAEEGGKGEKENGGGPPSGASPLHNISNSPLHATRSPLLGMG  dElk.PRO

758  CTSSSS----AAKILSPRRTAPRPRLGG------RGRPGRAGAIKAEAGPSAPPRALEGL  hElk2.PRO
797  SPRNQRLHQRGRSLITIRFINKRHRLNAACSLDRGSFEEPEPLEEEQSSGGKRPSLERL  dElk.PRO

808  -RLPPMPWNVPPDLSPRVVDGIED--------GCGSDQPKFSFRVGQSGPECSSSPSP-  hElk2.PRO
857  SDQVSTLHQDVA-QLSAEVRNAISALQEMTFTSNAMTSHSSLKFPPARSIPNISGVAGTR  dElk.PRO

857  ---GPESGILTV--------------PHGFSEARNT-  hElk2.PRO
916  SGVAVEHGLMGGVLAAAELAAMQRSSSHPPEVWGRDVQLPTSNTASSKAPSPVEPKKIMT  dElk.PRO

876  ------DILDKLRQAVTEISEQVL---QMREGLQSDRQAVQIVLAP-HREGP  hElk2.PRO
976  SRSSQTDFYRIDFPIFERFVIANPRLVLGLLGIEPAIKNEMDLLQKQTLQISENTIDE   dElk.PRO
```

FIG. 1B.

```
 918 CPRASGEGPCPAASTSGLLQPLCVDTFASSYCLQPPAGSVLSGT--WP----------- hElk2.PRO
1036 QVSPSDHNL-ASSKERLITSSAVTPGRIYPPLDDENSNDFRWTMKHSASHHSCCKS dElk.PRO

963 -------HPAPGPPPLMAPWPWGFPASQSSPWPRATAFWTSTDSEPP----------- hElk2.PRO
1092 TDALLSPEEQPPISILEVDATEAPSVQEVRSSKRSIRKSTSGNSSLSSSSSSNSCLVS dElk.PRO

1004 -ASGDI------CSEPSTPASPPPSE-------EGARTGPAEPVSQAEAT---STGEP hElk2.PRO
1152 QSTGNLTTNASVHCSNSSQSVASVATTRRASWKLQHSRSGEYRRLSEATAEYSPPAKTE dElk.PRO

1045 PFGSGG---------IALPQDPHSLEMVLIGCHGSGTVQ--------------- hElk2.PRO
1212 LBVAGVSYGGDEEESVELLGPRRNSRPILLGVSQNQGQAMNRFSAGDADKLEKGLRG dElk.PRO

1075 ----WTQEEGTGV hElk2.PRO
1272 LPSTRSLRDPSSK dElk.PRO
```

FIG. 1C.

SEQUENCE LISTING

```
<160> NUMBER OF SEQ ID NOS: 9

<210> SEQ ID NO 1
<211> LENGTH: 1083
<212> TYPE: PRT
<213> ORGANISM: Homo sapiens
<220> FEATURE:
<223> OTHER INFORMATION: human Elk (hElk; Eag (ether a go-go)-like K+
      gene) potassium channel monomer protein

<400> SEQUENCE: 1

Met Pro Ala Met Arg Gly Leu Leu Ala Pro Gln Asn Thr Phe Leu Asp
 1               5                  10                  15

Thr Ile Ala Thr Arg Phe Asp Gly Thr His Ser Asn Phe Val Leu Gly
            20                  25                  30

Asn Ala Gln Val Ala Gly Leu Phe Pro Val Val Tyr Cys Ser Asp Gly
        35                  40                  45

Phe Cys Asp Leu Thr Gly Phe Ser Arg Ala Glu Val Met Gln Arg Gly
    50                  55                  60

Cys Ala Cys Ser Phe Leu Tyr Gly Pro Asp Thr Ser Glu Leu Val Arg
65                  70                  75                  80

Gln Gln Ile Arg Lys Ala Leu Asp Glu His Lys Glu Phe Lys Ala Glu
                85                  90                  95

Leu Ile Leu Tyr Arg Lys Ser Gly Leu Pro Phe Trp Cys Leu Leu Asp
            100                 105                 110

Val Ile Pro Ile Lys Asn Glu Lys Gly Glu Val Ala Leu Phe Leu Val
        115                 120                 125

Ser His Lys Asp Ile Ser Glu Thr Lys Asn Arg Gly Gly Pro Asp Arg
    130                 135                 140

Trp Lys Glu Thr Gly Gly Gly Arg Arg Arg Tyr Gly Arg Ala Arg Ser
145                 150                 155                 160

Lys Gly Phe Asn Ala Asn Arg Arg Arg Ser Arg Ala Val Leu Tyr His
```

-continued

```
                165                 170                 175
Leu Ser Gly His Leu Gln Lys Gln Pro Lys Gly Lys His Lys Leu Asn
            180                 185                 190
Lys Gly Val Phe Gly Glu Lys Pro Asn Leu Pro Glu Tyr Lys Val Ala
            195                 200                 205
Ala Ile Arg Lys Ser Pro Phe Ile Leu Leu His Cys Gly Ala Leu Arg
            210                 215                 220
Ala Thr Trp Asp Gly Phe Ile Leu Leu Ala Thr Leu Tyr Val Ala Val
225                 230                 235                 240
Thr Val Pro Tyr Ser Val Cys Val Ser Thr Ala Arg Glu Pro Ser Ala
                245                 250                 255
Ala Arg Gly Pro Pro Ser Val Cys Asp Leu Ala Val Glu Val Leu Phe
            260                 265                 270
Ile Leu Asp Ile Val Leu Asn Phe Arg Thr Thr Phe Val Ser Lys Ser
            275                 280                 285
Gly Gln Val Val Phe Ala Pro Lys Ser Ile Cys Leu His Tyr Val Thr
            290                 295                 300
Thr Trp Phe Leu Leu Asp Val Ile Ala Ala Leu Pro Phe Asp Leu Leu
305                 310                 315                 320
His Ala Phe Lys Val Asn Val Tyr Phe Gly Ala His Leu Leu Lys Thr
                325                 330                 335
Val Arg Leu Leu Arg Leu Leu Arg Leu Leu Pro Arg Leu Asp Arg Tyr
            340                 345                 350
Ser Gln Tyr Ser Ala Val Val Leu Thr Leu Leu Met Ala Val Phe Ala
            355                 360                 365
Leu Leu Ala His Trp Val Ala Cys Val Trp Phe Tyr Ile Gly Gln Arg
            370                 375                 380
Glu Ile Glu Ser Ser Glu Ser Glu Leu Pro Glu Ile Gly Trp Leu Gln
385                 390                 395                 400
Glu Leu Ala Arg Arg Leu Glu Thr Pro Tyr Tyr Leu Val Gly Arg Arg
                405                 410                 415
Pro Ala Gly Gly Asn Ser Ser Gly Gln Ser Asp Asn Cys Ser Ser Ser
            420                 425                 430
Ser Glu Ala Asn Gly Thr Gly Leu Glu Leu Leu Gly Gly Pro Ser Leu
            435                 440                 445
Arg Ser Ala Tyr Ile Thr Ser Leu Tyr Phe Ala Leu Ser Ser Leu Thr
            450                 455                 460
Ser Val Gly Phe Gly Asn Val Ser Ala Asn Thr Asp Thr Glu Lys Ile
465                 470                 475                 480
Phe Ser Ile Cys Thr Met Leu Ile Gly Ala Leu Met His Ala Val Val
                485                 490                 495
Phe Gly Asn Val Thr Ala Ile Ile Gln Arg Met Tyr Ala Arg Arg Phe
            500                 505                 510
Leu Tyr His Ser Arg Thr Arg Asp Leu Arg Asp Tyr Ile Arg Ile His
            515                 520                 525
Arg Ile Pro Lys Pro Leu Lys Gln Arg Met Leu Glu Tyr Phe Gln Ala
            530                 535                 540
Thr Trp Ala Val Asn Asn Gly Ile Asp Thr Thr Glu Leu Leu Gln Ser
545                 550                 555                 560
Leu Pro Asp Glu Leu Arg Ala Asp Ile Ala Met His Leu His Lys Glu
                565                 570                 575
Val Leu Gln Leu Pro Leu Phe Glu Ala Ala Ser Arg Gly Cys Leu Arg
            580                 585                 590
```

```
Ala Leu Ser Leu Ala Leu Arg Pro Ala Phe Cys Thr Pro Gly Glu Tyr
        595                 600                 605
Leu Ile His Gln Gly Asp Ala Leu Gln Ala Leu Tyr Phe Val Cys Ser
        610                 615                 620
Gly Ser Met Glu Val Leu Lys Gly Gly Thr Val Leu Ala Ile Leu Gly
625                 630                 635                 640
Lys Gly Asp Leu Ile Gly Cys Glu Leu Pro Arg Arg Glu Gln Val Val
            645                 650                 655
Lys Ala Asn Ala Asp Val Lys Gly Leu Thr Tyr Cys Val Leu Gln Cys
            660                 665                 670
Leu Gln Leu Ala Gly Leu His Asp Ser Leu Ala Leu Tyr Pro Glu Phe
        675                 680                 685
Ala Pro Arg Phe Ser Arg Gly Leu Arg Gly Glu Leu Ser Tyr Asn Leu
        690                 695                 700
Gly Ala Gly Gly Ser Ala Glu Val Asp Thr Ser Ser Leu Ser Gly
705                 710                 715                 720
Asp Asn Thr Leu Met Ser Thr Leu Glu Glu Lys Glu Thr Asp Gly Glu
                725                 730                 735
Gln Gly Pro Thr Val Ser Pro Ala Pro Ala Asp Glu Pro Ser Ser Pro
            740                 745                 750
Leu Leu Ser Pro Gly Cys Thr Ser Ser Ser Ala Ala Lys Leu Leu
        755                 760                 765
Ser Pro Arg Arg Thr Ala Pro Arg Pro Arg Leu Gly Gly Arg Gly Arg
        770                 775                 780
Pro Gly Arg Ala Gly Ala Leu Lys Ala Glu Ala Gly Pro Ser Ala Pro
785                 790                 795                 800
Pro Arg Ala Leu Glu Gly Leu Arg Leu Pro Met Pro Trp Asn Val
                805                 810                 815
Pro Pro Asp Leu Ser Pro Arg Val Val Asp Gly Ile Glu Asp Gly Cys
            820                 825                 830
Gly Ser Asp Gln Pro Lys Phe Ser Phe Arg Val Gly Gln Ser Gly Pro
        835                 840                 845
Glu Cys Ser Ser Ser Pro Ser Pro Gly Pro Glu Ser Gly Leu Leu Thr
850                 855                 860
Val Pro His Gly Pro Ser Glu Ala Arg Asn Thr Asp Thr Leu Asp Lys
865                 870                 875                 880
Leu Arg Gln Ala Val Thr Glu Leu Ser Glu Gln Val Leu Gln Met Arg
            885                 890                 895
Glu Gly Leu Gln Ser Leu Arg Gln Ala Val Gln Leu Val Leu Ala Pro
        900                 905                 910
His Arg Glu Gly Pro Cys Pro Arg Ala Ser Gly Glu Gly Pro Cys Pro
        915                 920                 925
Ala Ser Thr Ser Gly Leu Leu Gln Pro Leu Cys Val Asp Thr Gly Ala
        930                 935                 940
Ser Ser Tyr Cys Leu Gln Pro Pro Ala Gly Ser Val Leu Ser Gly Thr
945                 950                 955                 960
Trp Pro His Pro Ala Pro Gly Pro Pro Leu Met Ala Pro Trp Pro
            965                 970                 975
Trp Gly Pro Pro Ala Ser Gln Ser Ser Pro Trp Pro Arg Ala Thr Ala
            980                 985                 990
Phe Trp Thr Ser Thr Ser Asp Ser Glu Pro Pro Ala Ser Gly Asp Leu
        995                 1000                1005
```

-continued

```
Cys Ser Glu Pro Ser Thr Pro Ala Ser Pro Pro Ser Glu Glu Gly
    1010                1015                1020

Ala Arg Thr Gly Pro Ala Glu Pro Val Ser Gln Ala Glu Ala Thr Ser
1025                1030                1035                1040

Thr Gly Glu Pro Pro Gly Ser Gly Gly Leu Ala Leu Pro Trp Asp
            1045                1050                1055

Pro His Ser Leu Glu Met Val Leu Ile Gly Cys His Gly Ser Gly Thr
        1060                1065                1070

Val Gln Trp Thr Gln Glu Glu Gly Thr Gly Val
    1075                1080

<210> SEQ ID NO 2
<211> LENGTH: 3249
<212> TYPE: DNA
<213> ORGANISM: Homo sapiens
<220> FEATURE:
<221> NAME/KEY: CDS
<222> LOCATION: (1)..(3249)
<223> OTHER INFORMATION: hElk

<400> SEQUENCE: 2
atgccggcca tgcggggcct cctggcgccg cagaacacct tcctggacac catcgctacg     60
cgcttcgacg gcacgcacag taacttcgtg ctgggcaacg cccaggtggc ggggctcttc    120
cccgtggtct actgctctga tggcttctgt gacctcacgg gcttctcccg ggctgaggtc    180
atgcagcggg gctgtgcctg ctccttcctt tatgggccag acaccagtga gctcgtccgc    240
caacagatcc gcaaggccct ggacgagcac aaggagttca ggctgagct gatcctgtac    300 cggaagagcg ggctcccgtt ctggtgtctc ctggatgtga tacccataaa gaatgagaaa    360
ggggaggtgg ctctcttcct agtctctcac aaggacatca gcgaaaccaa gaaccgaggg    420
ggccccgaca gatggaagga gacaggtggt ggccggcgcc gatatggccg gcacgatcc    480 aaaggcttca tgccaaccg gcggcggagc cgggccgtgc tctaccacct gtccgggcac    540
ctgcagaagc agcccaaggg caagcacaag ctcaataagg gggtgtttgg ggagaaacca    600
aacttgcctg agtacaaagt agccgccatc cggaagtcgc ccttcatcct gttgcactgt    660
ggggcactga gagccacctg ggatggcttc atcctgctcg ccacactcta tgtggctgtc    720
actgtgccct acagcgtgtg tgtgagcaca gcacgggagc ccagtgccgc cgcggcccg    780 cccagcgtct gtgacctggc cgtggaggtc ctcttcatcc ttgacattgt gctgaatttc    840
cgtaccacat tcgtgtccaa gtcgggccag gtggtgtttg ccccaaagtc catttgcctc    900
cactacgtca ccacctggtt cctgctggat gtcatcgcag cgctgccctt tgacctgcta    960
catgccttca aggtcaacgt gtacttcggg gcccatctgc tgaagacggt gcgcctgctg   1020
cgcctgctgc gcctgcttcc gcggctggac cggtactcgc agtacagcgc cgtggtgctg   1080
acactgctca tggccgtgtt cgccctgctc gcgcactggg tcgcctgcgt ctggttttac   1140
attggccagc gggagatcga gagcagcgaa tccgagctgc ctgagattgg ctggctgcag   1200
gagctggccc ccgactgga gactccctac tacctggtgg ccggaggcc agctggaggg   1260 aacagctccg gccagagtga caactgcagc agcagcagcg aggccaacgg gacggggctg   1320
gagctgctgg gcggcccgtc gctgcgcagc gcctacatca cctccctcta cttcgcactc   1380
agcagcctca ccagtgtggg cttcggcaac gtgtccgcca acacgacac cgagaagatc   1440 ttctccatct gcaccatgct catcggcgc ctgatgcacg cggtggtgtt tgggaacgtg   1500
acggccatca tccagcgcat gtacgcccgc cgctttctgt accacagccg cacgcgcgac   1560
```

-continued

```
ctgcgcgact acatccgcat ccaccgtatc cccaagcccc tcaagcagcg catgctggag    1620
tacttccagg ccacctgggc ggtgaacaat ggcatcgaca ccaccgagct gctgcagagc    1680
ctccctgacg agctgcgcgc agacatcgcc atgcacctgc acaaggaggt cctgcagctg    1740
ccactgtttg aggcggccag ccgcggctgc ctgcgggcac tgtctctggc cctgcggccc    1800
gccttctgca cgccgggcga gtacctcatc caccaaggcg atgccctgca ggccctctac    1860
tttgtctgct ctggctccat ggaggtgctc aagggtggca ccgtgctcgc catcctaggg    1920
aagggcgacc tgatcggctg tgagctgccc cggcgggagc aggtggtaaa ggccaatgcc    1980
gacgtgaagg ggctgacgta ctgcgtcctg cagtgtctgc agctggctgg cctgcacgac    2040
agccttgcgc tgtaccccga gtttgccccg cgcttcagtc gtggcctccg aggggagctc    2100
agctacaacc tgggtgctgg gggaggctct gcagaggtgg acaccagctc cctgagcggc    2160
gacaataccc ttatgtccac gctggaggag aaggagacag atggggagca gggccccacg    2220
gtctccccag ccccagctga tgagccctcc agccccctgc tgtcccctgg ctgcacctcc    2280
tcatcctcag ctgccaagct gctatcccca cgtcgaacag caccccggcc tcgtctaggt    2340
ggcagaggga ggccaggcag ggcaggggct ttgaaggctg aggctggccc ctctgctccc    2400
ccacgggccc tagaggggct acggctgccc cccatgccat ggaatgtgcc cccagatctg    2460
agccccaggg tagtagatgg cattgaagac ggctgtggct cggaccagcc caagttctct    2520
ttccgcgtgg gccagtctgg cccggaatgt agcagcagcc cctcccctgg accagagagc    2580
ggcctgctca ctgttcccca tgggcccagc gaggcaagga acacagacac actggacaag    2640
cttcggcagg cggtgacaga gctgtcagag caggtgctgc agatgcggga aggactgcag    2700
tcacttcgcc aggctgtgca gcttgtcctg gcgccccaca gggagggtcc gtgccctcgg    2760
gcatcgggag aggggccgtg cccagccagc acctccgggc ttctgcagcc tctgtgtgtg    2820
gacactgggg catcctccta ctgcctgcag ccccagctg gctctgtctt gagtgggact     2880
tggccccacc ctcgtccggg gcctcctccc ctcatggcac cctggccctg gggtccccca    2940
gcgtctcaga gctccccctg gcctcgagcc acagctttct ggacctccac ctcagactca    3000 gagcccctg cctcaggaga cctctgctct gagcccagca ccctgcctc cctcctcct      3060 tctgaggaag gggctaggac tgggcccgca gagcctgtga gccaggctga ggctaccagc    3120
actggagagc ccccaccagg gtcaggggc ctggccttgc cctgggaccc ccacagcctg    3180
gagatggtgc ttattggctg ccatggctct ggcacagtcc agtggaccca ggaagaaggc    3240
acagggtc                                                              3249
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      amplification primer

<400> SEQUENCE: 3
atgccggcca tgcggggcct cct                                              23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      amplification primer -continued

```
<400> SEQUENCE: 4
agatggcagc acacctggca acgctg                                          26

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 5
gcccatctgc tgaagacggt gcgc                                            24

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 6
cgaagcccac gctggtgagg ctgctg                                          26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:genomic
      localization amplification hElk specific
      oligonucleotide

<400> SEQUENCE: 7
cacctgggat ggcttcatcc tgctc                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:genomic
      localization amplification hElk specific
      oligonucleotide

<400> SEQUENCE: 8
aaacaccacc tggcccgact tggac                                           25

<210> SEQ ID NO 9
<211> LENGTH: 1284
<212> TYPE: PRT
<213> ORGANISM: Drosophila melanogaster
<220> FEATURE:
<223> OTHER INFORMATION: Drosophila Elk (dElk; Eag (ether a go-go)-like
      K+ gene) protein

<400> SEQUENCE: 9
```

Met Pro Ala Arg Lys Gly Leu Leu Ala Pro Gln Asn Thr Phe Leu Asp
 1               5                  10                  15

Thr Ile Ala Thr Arg Phe Asp Gly Thr His Ser Asn Phe Val Leu Gly
            20                  25                  30

Asn Ala Gln Ala Asn Gly Asn Pro Ile Val Tyr Cys Ser Asp Gly Phe
        35                  40                  45

```
Val Asp Leu Thr Gly Tyr Ser Arg Ala Gln Ile Met Gln Lys Gly Cys
    50                  55                  60

Ser Cys His Phe Leu Tyr Gly Pro Asp Thr Lys Glu Glu His Lys Gln
65                  70                  75                  80

Gln Ile Glu Lys Ser Leu Ser Asn Lys Met Glu Leu Lys Leu Glu Val
                85                  90                  95

Ile Phe Tyr Lys Lys Glu Gly Ala Pro Phe Trp Cys Leu Phe Asp Ile
                100                 105                 110

Val Pro Ile Lys Asn Glu Lys Arg Asp Val Val Leu Phe Leu Ala Ser
                115                 120                 125

His Lys Asp Ile Thr His Thr Lys Met Leu Glu Met Asn Val Asn Glu
        130                 135                 140

Glu Cys Asp Ser Val Phe Ala Leu Thr Ala Ala Leu Leu Gly Ala Arg
145                 150                 155                 160

Phe Arg Ala Gly Ser Asn Ala Gly Met Leu Gly Leu Gly Gly Leu Pro
                165                 170                 175

Gly Leu Gly Gly Pro Ala Ala Ser Asp Gly Asp Thr Glu Ala Gly Glu
                180                 185                 190

Gly Asn Asn Leu Asp Val Pro Ala Gly Cys Asn Met Gly Arg Arg Arg
                195                 200                 205

Ser Arg Ala Val Leu Tyr Gln Leu Ser Gly His Tyr Lys Pro Glu Lys
    210                 215                 220

Gly Gly Val Lys Thr Lys Leu Lys Leu Gly Asn Asn Phe Met His Ser
225                 230                 235                 240

Thr Glu Ala Pro Phe Pro Glu Tyr Lys Thr Gln Ser Ile Lys Lys Ser
                245                 250                 255

Arg Leu Ile Leu Pro His Tyr Gly Val Phe Lys Gly Ile Trp Asp Trp
                260                 265                 270

Val Ile Leu Val Ala Thr Phe Tyr Val Ala Leu Met Val Pro Tyr Asn
            275                 280                 285

Ala Ala Phe Ala Lys Ala Asp Arg Gln Thr Lys Val Ser Asp Val Ile
        290                 295                 300

Val Glu Ala Leu Phe Ile Val Asp Ile Leu Leu Asn Phe Arg Thr Thr
305                 310                 315                 320

Phe Val Ser Arg Lys Gly Glu Val Val Ser Asn Ser Lys Gln Ile Ala
                325                 330                 335

Ile Asn Tyr Leu Arg Gly Trp Phe Ala Leu Asp Leu Leu Ala Ala Leu
                340                 345                 350

Pro Phe Asp His Leu Tyr Ala Ser Asp Leu Tyr Asp Gly Glu Asp Ser
                355                 360                 365

His Ile His Leu Val Lys Leu Thr Arg Leu Leu Arg Leu Ala Arg Leu
        370                 375                 380

Leu Gln Lys Ile Asp Arg Tyr Ser Gln His Thr Ala Met Ile Leu Thr
385                 390                 395                 400

Leu Leu Met Phe Ser Phe Thr Leu Ala Ala His Trp Leu Ala Cys Ile
                405                 410                 415

Trp Tyr Val Ile Ala Val Lys Glu Tyr Glu Trp Phe Pro Glu Ser Asn
                420                 425                 430

Ile Gly Trp Leu Gln Leu Leu Ala Glu Arg Lys Asn Ala Ser Val Ala
            435                 440                 445

Ile Leu Thr Thr Ala Glu Thr Tyr Ser Thr Ala Leu Tyr Phe Thr Phe
        450                 455                 460

Thr Ser Leu Thr Ser Val Gly Phe Gly Asn Val Ser Ala Asn Thr Thr
```

```
                465                 470                 475                 480
Ala Glu Lys Val Phe Thr Ile Ile Met Met Leu Ile Gly Ala Leu Met
                    485                 490                 495
His Ala Val Val Phe Gly Asn Val Thr Ala Ile Ile Gln Arg Met Tyr
                500                 505                 510
Ser Arg Arg Ser Leu Tyr Glu Ser Lys Trp Arg Asp Leu Lys Asp Phe
                515                 520                 525
Val Ala Leu His Asn Met Pro Lys Glu Leu Lys Gln Arg Ile Glu Asp
                530                 535                 540
Tyr Phe Gln Thr Ser Trp Ser Leu Ser His Gly Ile Asp Ile Tyr Glu
545                 550                 555                 560
Thr Leu Arg Glu Phe Pro Glu Glu Leu Arg Gly Asp Val Ser Met His
                    565                 570                 575
Leu His Arg Glu Ile Leu Gln Leu Pro Ile Phe Glu Ala Ala Ser Gln
                580                 585                 590
Gly Cys Leu Lys Leu Leu Ser Leu His Ile Lys Thr Asn Phe Cys Ala
            595                 600                 605
Pro Gly Glu Tyr Leu Ile His Lys Gly Asp Ala Leu Asn Tyr Ile Tyr
        610                 615                 620
Tyr Leu Cys Asn Gly Ser Met Glu Val Ile Lys Asp Asp Met Val Val
625                 630                 635                 640
Ala Ile Leu Gly Lys Gly Asp Leu Val Gly Ser Asp Ile Asn Val His
                645                 650                 655
Leu Val Ala Thr Ser Asn Gly Gln Met Thr Ala Thr Thr Asn Ser Ala
            660                 665                 670
Gly Gln Asp Val Val Val Arg Ser Ser Asp Ile Lys Ala Leu Thr
        675                 680                 685
Tyr Cys Asp Leu Lys Cys Ile His Met Gly Gly Leu Val Glu Val Leu
    690                 695                 700
Arg Leu Tyr Pro Glu Tyr Gln Gln Gln Phe Ala Asn Asp Ile Gln His
705                 710                 715                 720
Asp Leu Thr Cys Asn Leu Arg Glu Gly Tyr Glu Asn Gln Asp Ser Asp
                725                 730                 735
Ile Gly Pro Ser Phe Pro Leu Pro Ser Ile Ser Glu Asp Asp Glu Asn
                740                 745                 750
Arg Glu Glu Ala Glu Glu Gly Gly Lys Gly Glu Lys Glu Asn Gly Gly
            755                 760                 765
Gly Pro Pro Ser Gly Ala Ser Pro Leu His Asn Ile Ser Asn Ser Pro
        770                 775                 780
Leu His Ala Thr Arg Ser Pro Leu Leu Gly Met Gly Ser Pro Arg Asn
785                 790                 795                 800
Gln Arg Leu His Gln Arg Gly Arg Ser Leu Ile Thr Leu Arg Glu Thr
                805                 810                 815
Asn Lys Arg His Arg Thr Leu Asn Ala Ala Cys Ser Leu Asp Arg Gly
                820                 825                 830
Ser Phe Glu Glu Pro Glu Pro Leu Glu Glu Gln Ser Ser Gly Gly
            835                 840                 845
Lys Arg Pro Ser Leu Glu Arg Leu Asp Ser Gln Val Ser Thr Leu His
        850                 855                 860
Gln Asp Val Ala Gln Leu Ser Ala Glu Val Arg Asn Ala Ile Ser Ala
865                 870                 875                 880
Leu Gln Glu Met Thr Phe Thr Ser Asn Ala Met Thr Ser His Ser Ser
                885                 890                 895
```

```
Leu Lys Phe Pro Pro Ala Arg Ser Ile Pro Asn Ile Ser Gly Val Ala
            900                 905                 910

Gly Thr Arg Ser Gly Val Ala Val Glu His Gly Leu Met Gly Gly Val
        915                 920                 925

Leu Ala Ala Ala Glu Leu Ala Ala Met Gln Arg Ser Ser His Pro
    930                 935                 940

Pro Glu Val Trp Gly Arg Asp Val Gln Leu Pro Thr Ser Asn Thr Ala
945                 950                 955                 960

Ser Ser Lys Ala Pro Ser Pro Val Glu Pro Lys Lys Thr Met Thr Ser
                965                 970                 975

Arg Ser Ser Gln Thr Asp Phe Tyr Arg Ile Asp Phe Pro Thr Phe Glu
            980                 985                 990

Arg Phe Val Leu Ala Asn Pro Arg Leu Val Leu Gly Leu Leu Gly Ile
        995                 1000                1005

Glu Pro Ala Ile Lys Asn Glu Met Asp Leu Leu Gln Gln Lys Gln Thr
    1010                1015                1020

Leu Gln Ile Ser Pro Leu Asn Thr Ile Asp Glu Cys Val Ser Pro Ser
1025                1030                1035                1040

Asp His Asn Leu Ala Ser Ser Lys Glu Arg Leu Ile Thr Ser Ser Ala
                1045                1050                1055

Val Pro Thr Pro Gly Arg Ile Tyr Pro Pro Leu Asp Asp Glu Asn Ser
            1060                1065                1070

Asn Asp Phe Arg Trp Thr Met Lys His Ser Ala Ser His His Ser Cys
        1075                1080                1085

Cys Lys Ser Thr Asp Ala Leu Leu Ser Pro Glu Glu Gln Pro Pro Ile
    1090                1095                1100

Ser Ile Leu Pro Val Asp Ala Thr Pro Ala Pro Ser Val Gln Glu Val
1105                1110                1115                1120

Arg Ser Ser Lys Arg Ser Ile Arg Lys Ser Thr Ser Gly Ser Asn Ser
                1125                1130                1135

Ser Leu Ser Ser Ser Ser Ser Ser Asn Ser Cys Leu Val Ser Gln
            1140                1145                1150

Ser Thr Gly Asn Leu Thr Thr Thr Asn Ala Ser Val His Cys Ser Asn
        1155                1160                1165

Ser Ser Gln Ser Val Ala Ser Val Ala Thr Thr Arg Arg Ala Ser Trp
    1170                1175                1180

Lys Leu Gln His Ser Arg Ser Gly Glu Tyr Arg Arg Leu Ser Glu Ala
1185                1190                1195                1200

Thr Ala Glu Tyr Ser Pro Pro Ala Lys Thr Pro Leu Pro Val Ala Gly
                1205                1210                1215

Val Ser Tyr Gly Gly Asp Glu Glu Ser Val Glu Leu Leu Gly Pro
            1220                1225                1230

Arg Arg Asn Ser Arg Pro Ile Leu Leu Gly Val Ser Gln Asn Gln Gly
        1235                1240                1245

Gln Gly Gln Ala Met Asn Phe Arg Phe Ser Ala Gly Asp Ala Asp Lys
    1250                1255                1260

Leu Glu Lys Gly Leu Arg Gly Leu Pro Ser Thr Arg Ser Leu Arg Asp
1265                1270                1275                1280

Pro Ser Ser Lys
```

ANTIBODIES TO HUMAN ELK, A VOLTAGE-GATED POTASSIUM CHANNEL SUBUNIT

CROSS-REFERENCES TO RELATED APPLICATIONS

This application is a division of U.S. Ser. No. 10/160,224, filed May 28, 2002, now U.S. Pat. No. 6,833,440, which is a division of U.S. Ser. No. 09/343,494, filed Jun. 30, 1999, now U.S. Pat. No. 6,413,741, which claims the benefit of U.S. Ser. No. 60/091,469, filed Jul. 1, 1998, and U.S. Ser. No. 60/116,621, filed Jan. 21, 1999, all of which are herein incorporated by reference in their entirety.

STATEMENT AS TO RIGHTS TO INVENTIONS MADE UNDER FEDERALLY SPONSORED RESEARCH AND DEVELOPMENT

Not applicable

FIELD OF THE INVENTION

The invention provides isolated nucleic acid and amino acid sequences of hElk, antibodies to hElk, methods of detecting hElk, methods of screening for voltage-gated potassium channel activators and inhibitors using biologically active hElk, and kits for screening for activators and inhibitors of voltage gated potassium channels comprising hElk.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35 (7):805-829 (1997)). Three of these families (Kv, Eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94 (25):14066-71 (1997)) and are gated by both voltage and calcium or pH (Schreiber et al., *J. Biol. Chem.* 273:3509-16 (1998)). Another family, the inward rectifier potassium channels (Kir), belong to a structural family containing 2 transmembrane domains (see, e.g., Lagrutta et al., *Jpn. Heart. J.* 37:651-660 1996)), and an eighth functionally diverse family (TP, or "two-pore") contains 2 tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These beta subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625-633 (1996); Shi et al., *Neuron* 16 (4):843-852 (1996)). In another example, the KQT family beta subunit, minK, primarily changes activation kinetics (Sanguinetti et al., *Nature* 384: 80-83 (1996)).

The Kv superfamily of voltage-gated potassium channels includes both heteromeric and homomeric channels that are typically composed of four subunits. Voltage-gated potassium channels have been found in a wide variety of tissues and cell types and are involved in processes such as neuronal integration, cardiac pacemaking, muscle contraction, hormone section, cell volume regulation, lymphocyte differentiation, and cell proliferation (see, e.g., Salinas et al., *J. Biol. Chem.* 39:24371-24379 (1997)).

A family of voltage-gated potassium genes, known as the "Eag" or ether à go-go family, was identified on the basis of a *Drosophila* behavioral mutation with a leg-shaking phenotype (see, e.g., Warmke & Ganetzky, *Proc. Nat'l Acad. Sci. USA* 91:3438-3442 (1994)). Family members from *Drosophila* and vertebrates have been cloned and fall into three subfamilies. One such subfamily is called the Eag subfamily and is represented, e.g., by *Drosophila* Eag (Warmke et al., *Science* 252:1560-1562 (1991); Bruggemann et al., *Nature* 365:445-447 (1993)), and rat, mouse, human, and bovine Eags (Ludwig et al., *EMBO J.* 13:4451-4458 (1994); Robertson et al. *Neuropharmacology* 35:841-850 (1996); Occhiodoro et al., *FEBS Letters* 434:177-182 (1998); Shi et al., *J. Physiol.* 115.3:675-682 (1998); Frings et al., *J. Gen Physiol.* 111:583-599 (1998)). A second subfamily, the Erg or "Eag-related gene" family is represented, e.g., by human erg (Shi et al., *J. Neurosci.* 17:9423-9432 (1997)). Finally, a third subfamily, the Elk or "Eag-like $K^+$ gene" is represented, e.g., by *Drosophila* Elk (Warmke et al., *Proc. Natl. Acad. Sci.* 91:3438-3442 (1994)).

SUMMARY OF THE INVENTION

The present invention thus provides for the first time human Elk, a polypeptide monomer that is an alpha subunit of an voltage-gated potassium channel. hElk has not been previously cloned or identified, and the present invention provides the nucleotide and amino acid sequence of hElk. Furthermore, the gene encoding hElk has been mapped to chromosome 12.

In one aspect, the present invention provides an isolated nucleic acid encoding a polypeptide monomer comprising an alpha subunit of a potassium channel, the polypeptide monomer: (i) having the ability to form, with at least one additional Elk alpha subunit, a potassium channel having the characteristic of voltage gating; (ii) having a monomer P-S6 region that has greater than 80%, preferably 85, 90, or 95% amino acid sequence identity to an hElk P-S6 region; and (iii) specifically binding to polyclonal antibodies generated against SEQ ID NO:1.

In another embodiment, the present invention provides an isolated nucleic acid encoding a polypeptide monomer comprising an alpha subunit of a potassium channel, the polypeptide monomer: (i) having the ability to form, with at least one additional Elk alpha subunit, a potassium channel having the characteristic of voltage gating; (ii) having an extended P-S6 region that has greater than 80%, preferably 85, 90, or 95% amino acid sequence identity to an hElk extended P-S6 region; and (iii) specifically binding to polyclonal antibodies generated against SEQ ID NO:1.

In one embodiment, the nucleic acid encodes human Elk. In another embodiment, the nucleic acid encodes SEQ ID NO:1. In another embodiment, the nucleic acid has a nucleotide sequence of SEQ ID NO:2.

In one embodiment, the nucleic acid is amplified by primers that selectively hybridize under stringent hybridization conditions to the same sequence as the primer sets selected from the group consisting of:

```
ATGCCGGCCATGCGGGCCTCCT,         (SEQ ID NO:3)

AGATGGCAGCACACCTGGCAACGCTG      (SEQ ID NO:4)
and

GCCCATCTGCTGAAGACGGTGCGC,       (SEQ ID NO:5)

CGAAGCCCACGCTGGTGAGGCTGCTG.     (SEQ ID NO:6)
```

In one embodiment, the nucleic acid encodes a polypeptide monomer having a molecular weight of between about 120 kDa to about 130 kDa. In another embodiment, the polypeptide monomer comprises an alpha subunit of a homomeric voltage-gated potassium channel. In another embodiment, the polypeptide monomer comprises an alpha subunit of a heteromeric voltage-gated potassium channel.

In another embodiment, the nucleic acid selectively hybridizes under moderately stringent hybridization conditions to a nucleotide sequence of SEQ ID NO:2.

In another aspect, the present invention provides an isolated nucleic acid encoding a polypeptide monomer, wherein the nucleic acid specifically hybridizes under highly stringent conditions to SEQ ID NO:2.

In another aspect, the present invention provides an isolated polypeptide monomer comprising an alpha subunit of a potassium channel, the polypeptide monomer: (i) having the ability to form, with at least one additional Elk alpha subunit a potassium channel having the characteristic of voltage gating; (ii) having a monomer P-S6 region that has greater than 80% amino acid sequence identity to an hElk P-S6 region; and (iii) specifically binding to polyclonal antibodies generated against SEQ ID NO:1.

In one embodiment, the polypeptide monomer has an amino acid sequence of human Elk. In another embodiment, the polypeptide monomer has an amino acid sequence of SEQ ID NO:1.

In another aspect, the present invention provides an antibody that selectively binds to the polypeptide monomer described above.

In another aspect, the present invention provides an expression vector comprising the nucleic acid encoding the polypeptide monomer described above.

In another aspect, the present invention provides a host cell transfected with the expression vector described above.

In another aspect, the present invention provides a method for identifying a compound that increases or decreases ion flux through an voltage-gated potassium channel, the method comprising the steps of: (i) contacting the compound with a eukaryotic host cell or cell membrane in which has been expressed a polypeptide monomer comprising an alpha subunit of a potassium channel, the polypeptide monomer: (a) having the ability to form, with at least one additional Elk alpha subunit, a potassium channel having the characteristic of voltage gating; (b) having a monomer P-S6 region that has greater than 80% amino acid sequence identity to an hElk P-S6 region; and (c) specifically binding to polyclonal antibodies generated against SEQ ID NO:1; and (ii) determining the functional effect of the compound upon the cell or cell membrane expressing the potassium channel.

In one embodiment, the increased or decreased flux of ions is determined by measuring changes in current or voltage. In another embodiment, the polypeptide monomer polypeptide is recombinant. In another embodiment, the potassium channel is homomeric.

In another embodiment, the present invention provides a method of detecting the presence of hElk in human tissue, the method comprising the steps of: (i) isolating a biological sample; (ii) contacting the biological sample with a hElk-specific reagent that selectively associates with hElk; and, (iii) detecting the level of hElk-specific reagent that selectively associates with the sample.

In one embodiment, the hElk-specific reagent is selected from the group consisting of: hElk specific antibodies, hElk specific oligonucleotide primers, and hElk nucleic acid probes.

In another aspect, the present invention provides, in a computer system, a method of screening for mutations of hElk genes, the method comprising the steps of: (i) entering into the computer a first nucleic acid sequence encoding an voltage-gated potassium channel protein having a nucleotide sequence of SEQ ID NO:2, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In another aspect, the present invention provides, in a computer system, a method for identifying a three-dimensional structure of hElk polypeptides, the method comprising the steps of: (i) entering into the computer an amino acid sequence of at least 25, 50 or 100 amino acids of a potassium channel monomer or at least 75, 150 or 300 nucleotides of a nucleic acid encoding the polypeptide, the polypeptide having an amino acid sequence of SEQ ID NO:1, and conservatively modified versions thereof; and (ii) generating a three-dimensional structure of the polypeptide encoded by the amino acid sequence.

In one embodiment, the amino acid sequence is a primary structure and wherein said generating step includes the steps of: (i) forming a secondary structure from said primary structure using energy terms determined by the primary structure; and (ii) forming a tertiary structure from said secondary structure using energy terms determined by said secondary structure. In another embodiment, the generating step includes the step of forming a quaternary structure from said tertiary structure using anisotropic terms determined by the tertiary structure. In another embodiment, the methods further comprises the step of identifying regions of the three-dimensional structure of the protein that bind to ligands and using the regions to identify ligands that bind to the protein.

BRIEF DESCRIPTION OF THE DRAWINGS

FIG. 1. Amino acid alignment of *Drosophila* (SEQ ID NO:9) and human (SEQ ID NO:1) Elk. Identical residues are shaded. The numbers at the right margin indicate amino acid position. Gaps in alignment are represented by dashes.

DETAILED DESCRIPTION OF THE INVENTION

I. Introduction

Figure 2:
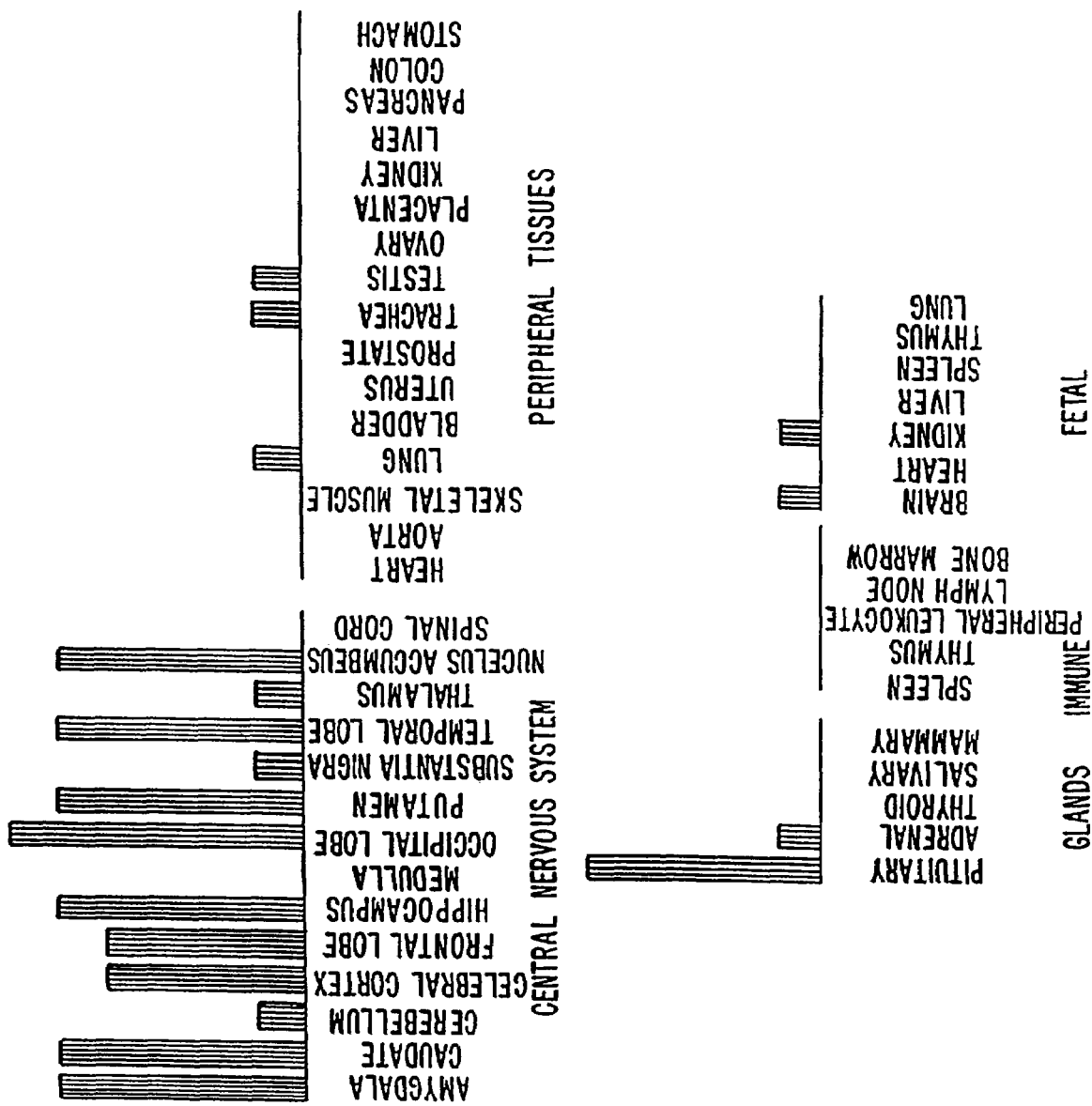
FIG. 2. mRNA distribution of human Elk. The height of the bars indicates relative expression levels. Data was generated using mRNA dot blots. The hElk probe used here detects a single band of approximately 4.5 Kb in northern blot analysis. Tissue names are given below the bars. High levels of expression are found in CNS tissues and the pituitary gland.

The present invention provides for the first time a nucleic acid encoding human Elk, identified and cloned from human tissue. This polypeptide monomer is a member of the "Kv" superfamily of potassium channel monomers, the "Eag" (ether a go-go) family of potassium channel monomer, and the "Elk" subfamily of potassium channel monomers. Members of this subfamily are polypeptide monomers that are subunits of voltage-gated potassium channels having six transmembrane regions (K=potassium, v=voltage-gated). Voltage-gated potassium channels have significant roles in maintaining the resting potential and in controlling excitability of a cell.

The invention also provides methods of screening for activators and inhibitors of voltage-gated potassium channels that contain a hElk subunit. Such modulators of voltage-gated channel activity are useful for treating disorders involving abnormal ion flux, e.g., disorders of the endocrine system, CNS disorders such as migraines, hearing and vision problems, psychotic disorders, seizures, psychotic disorders, and as neuroprotective agents (e.g., to prevent stroke).

Furthermore, the invention provides assays for hElk activity where hElk acts as a direct or indirect reporter molecule. Such uses of hElk as a reporter molecule in assay and detection systems have broad applications, e.g., hElk can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, hElk can be used as an indicator of current flow in a particular direction (e.g., outward or inward potassium flow), and in another embodiment, hElk can be used as an indirect reporter via attachment to a second reporter molecule such as green fluorescent protein.

The invention also provides for methods of detecting hElk nucleic acid and protein expression, allowing investigation of the channel diversity provided by hElk, as well as diagnosis of disease caused by abnormal ion flux, e.g., endocrine system disorders, CNS disorders such as migraines, hearing and vision problems, psychotic disorders, and seizures. In particular, hElk has been mapped to chromosome 12 (see Example III). hElk can therefore be used as a marker for diagnosis of diseases linked to the hElk gene on chromosome 12.

Finally, the invention provides for a method of screening for mutations of hElk genes or proteins. The invention includes, but is not limited to, methods of screening for mutations in hElk with the use of a computer. Similarly, the invention provides for methods of identifying the three-dimensional structure of hElk, as well as the resulting computer readable images or data that comprise the three dimensional structure of hElk. Other methods for screening for mutations of hElk genes or proteins include high density oligonucleotide arrays, PCR, immunoassays and the like.

Functionally, hElk is an alpha subunit of an voltage-gated potassium channel. Typically, such voltage-gated channels are heteromeric or homomeric and contain four alpha subunits or monomers each with six transmembrane domains. Heteromeric Elk channels can comprise one or more hElk alpha subunits along with one or more additional alpha subunits from the Kv superfamily or the Eag family, preferably from the Elk subfamily. hElk channels may also be homomeric. In addition, such channels may comprise one or more auxiliary beta subunits. The presence of hElk in an voltage-gated potassium channel may also modulate the activity of the heteromeric channel and thus enhance channel diversity. Channel diversity is also enhanced with alternatively spliced forms of hElk.

Structurally, the nucleotide sequence of human Elk (SEQ ID NO:2) encodes a polypeptide monomer of approximately 1083 amino acids with a predicted molecular weight of approximately 125 kDa (SEQ ID NO:1) and a predicted range of 120-130 kDa. In particular, the amino acid sequence of hElk has a "pore to S6" or "P-S6" region (approximately amino acids 452 to 514, see, e.g., amino acids 452-514 of SEQ ID NO:1, hElk) that has a conserved amino acid sequence. Another conserved amino acid region is the extended P-S6 region, which includes some cytoplasmic sequence, from amino acids 452-710. Related Elk genes from other species share at least about 80%, preferably 85, 90 or 95% amino acid identity in these regions.

The present invention also provide polymorphic variants of the hElk depicted in SEQ ID NO:1: variant #1, in which a valine residue is substituted for the isoleucine residue at amino acid position 1064; variant #2, in which an isoleucine residue is substituted for the leucine residue at amino acid position 1060; and variant #3, in which a serine residue is substituted for the alanine residue at amino acid position 744.

Specific regions of hElk nucleotide and amino acid sequence may be used to identify polymorphic variants, interspecies homologs, and alleles of hElk. This identification can be made in vitro, e.g., under stringent hybridization conditions and sequencing, or by using the sequence information in a computer system for comparison with other nucleotide sequences, or using antibodies raised to hElk. Typically, identification of polymorphic variants, orthologs, and alleles of hElk is made by comparing the amino acid sequence (or the nucleic acid encoding the amino acid sequence) of the P-S6 region (approximately amino acids 452-514 of hElk, see SEQ ID NO:1 for example), or by comparing the amino acid sequence of the extended P-S6 region (amino acids 452-710). Amino acid identity of approximately at least 80% or above, preferably 85%, most preferably 90-95% or above in the P-S6 region or the extended P-S6 region typically demonstrates that a protein is a polymorphic variant, interspecies homolog, or allele of hElk. Sequence comparison can be performed using any of the sequence comparison algorithms discussed below.

Polymorphic variants, interspecies homologs, and alleles of hElk can be confirmed by expressing or co-expressing the putative hElk polypeptide monomer and examining whether it forms a potassium channel with Elk/Kv/Eag functional characteristics, such as voltage-gating. This assay is used to demonstrate that a protein having about 80% or greater, preferably 85%, 90%, or 95% or greater amino acid identity to the "pore-S6" region of hElk shares the same functional characteristics as hElk and is therefore a species of hElk. Typically, hElk having the amino acid sequence of SEQ ID NO:1 is used as a positive control in comparison to the putative hElk protein to demonstrate the identification of a polymorphic variant, ortholog, or allele of hElk.

hElk nucleotide and amino acid sequence information may also be used to construct models of voltage-gated potassium channels in a computer system. These models are subsequently used to identify compounds that can activate or inhibit voltage-gated potassium channels comprising hElk. Such compounds that modulate the activity of channels comprising hElk can be used to investigate the role of hElk in modulation of channel activity and in channel diversity.

The isolation of biologically active hElk for the first time provides a means for assaying for inhibitors and activators of voltage-gated potassium channels that comprise hElk subunits. Biologically active hElk is useful for testing inhibitors and activators of voltage-gated potassium channels comprising subunits of hElk and other Kv members using in vivo and in vitro expression that measure, e.g., changes in voltage or current. Such activators and inhibitors identified using an voltage-gated potassium channel comprising at least one hElk subunit, preferably four Elk subunits, can be used to further study voltage gating, channel kinetics and conductance properties of potassium channels. Such activators and inhibitors are useful as pharmaceutical agents for treating diseases involving abnormal ion flux, e.g., endocrine and CNS disorders, as described above. Methods of detecting hElk and expression of channels comprising hElk are also useful for diagnostic applications for diseases involving abnormal ion flux, e.g., CNS disorders, endocrine disorders, and other disorders as described above. For example, chromosome localization of the gene encoding human Elk can be used to identify diseases caused by and associated with hElk. Methods of detecting hElk are also useful for examining the role of hElk in channel diversity and modulation of channel activity.

II. Definitions

As used herein, the following terms have the meanings ascribed to them unless specified otherwise.

The phrase "voltage-gated" activity or "voltage-gating" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the membrane potential for potassium ($E_K$) in typical cells. $E_K$, or the membrane potential for potassium, depends on the relative concentrations of potassium found inside and outside the cell membrane, and is typically between −60 and −100 mV for mammalian cells. $E_K$ is the membrane potential at which there is no net flow of potassium ion because the electrical potential (i.e., voltage potential) driving potassium influx is balanced by the concentration gradient (the [K$^+$] potential) directing potassium efflux. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Normer, in *Potassium Channels*, pp. 40-60 (Cook, ed., 1990)). The characteristic of voltage gating can be measured by a variety of techniques for measuring changes in current flow and ion flux through a channel, e.g., by changing the [K$^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

"Homomeric channel" refers to an hElk channel composed of identical alpha subunits, whereas "heteromeric channel" refers to an hElk channel composed of at least one hElk alpha subunit plus at least one other different type of alpha subunit from a related gene family such as the Kv superfamily or the Eag family, preferably from the Elk subfamily. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "P-S6 region" (pore to S6) refers to the region of hElk that structurally identifies this particular protein (approximately amino acids 452-514 of hElk, see SEQ ID NO:1). The phrase "extended P-S6 region" refers to another region of hElk that can also be used to structurally identify this protein (approximately amino acids 452-710 of hElk, see SEQ ID NO:1). These regions can be used to identify hElk polymorphic variants, orthologs, and hElk alleles of hElk, through amino acid sequence identity comparison using a sequence comparison algorithm such as BLASTP or PILEUP. P-S6 comprises the pore region arid the S6 transmembrane region, while the extended P-S6 region includes cytoplasmic sequences. (see, e.g., Ackerman & Clapham, *New Engl. J. Med.* 336:1575-1586 (1997); Jan & Jan, *Annu. Rev. Neurosci.* 20:91-123 (1997)).

"hElk" refers to a polypeptide that is a subunit or monomer of an voltage-gated potassium channel, a member of the Elk subfamily, a member of the Eag family, and a member of the Kv superfamily of potassium channel monomers. When hElk is part of a potassium channel, either a homomeric or heteromeric potassium channel, the channel has voltage-gated activity. The term hElk therefore refers to polymorphic variants, alleles, mutants, and interspecies homologs that: (1) have a P-S6 region or an extended P-S6 region that has greater than about 80% amino acid sequence identity, preferably about 85, 90, or 95% amino acid sequence identity, to a hElk P-S6 region or an extended P-S6 region; (2) bind to antibodies raised against an immunogen comprising an amino acid sequence selected from the group consisting of SEQ ID NO:1, amino acids 452-514 of SEQ ID NO:1, amino acids 452-710 of SEQ ID NO:1 and conservatively modified variants thereof; (3) specifically hybridize under stringent hybridization conditions to a sequence selected from the group consisting of SEQ ID NO:2, the nucleotide sequence encoding amino acids 452-514 of SEQ ID NO:1, the nucleotide sequence encoding amino acids 452-710 of SEQ ID NO:1, and conservatively modified variants thereof; or (4) are amplified by primers that specifically hybridize under stringent hybridization conditions to the same sequence as a primer set consisting of SEQ ID NO:3 and SEQ ID NO:4 or SEQ ID NO:5 and SEQ ID NO:6.

The phrase "functional effects" in the context of assays for testing compounds affecting a channel comprising hElk includes the determination of any parameter that is indirectly or directly under the influence of the channel. It includes changes in ion flux and membrane potential, and also includes other physiologic effects such as increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., potassium, rubidium, sodium. Preferably, the term refers to the functional effect of the compound on the channels comprising hElk, e.g., changes in ion flux including radioisotopes, current amplitude, membrane potential, current flow, transcription, protein binding, phosphorylation, dephosphorylation, second messenger concentrations (cAMP, cGMP, $Ca^{2+}$, $IP_3$) and other physiological effects such as hormone and neurotransmitter release, as well as changes in voltage and current. Such functional effects can be measured by any means known to those skilled in the art, e.g., patch clamping, voltage-sensitive dyes, whole cell currents, radioisotope efflux, inducible markers, and the like.

"Inhibitors," "activators" or "modulators" of voltage-gated potassium channels comprising hElk refer to inhibitory or activating molecules identified using in vitro and in vivo assays for hElk channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing hElk in cells or cell membranes and then measuring flux of ions through the channel and determining changes in polarization (i.e., electrical potential). Alternatively, cells expressing endogenous hElk channels can be used in such assays. To examine the extent of inhibition, samples or assays comprising an hElk channel are treated with a potential activator or inhibitor and are compared to control samples without the inhibitor. Control samples (untreated with inhibitors) are assigned a relative hElk activity value of 100%. Inhibition of channels comprising hElk is achieved when the hElk activity value relative to the control is about 90%, preferably 50%, more preferably 25-0%. Activation of channels comprising hElk is achieved when the hElk activity value relative to the control is 110%, more preferably 150%, most preferably at least 200-500% higher or 1000% or higher.

"Biologically active" hElk refers to hElk that has the ability to form a potassium channel having the characteristic of voltage-gating tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated hElk nucleic acid is separated from open reading frames that flank the hElk gene and encode proteins other than hElk. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition. An example of potassium channel splice variants is discussed in Leicher, et al., *J. Biol. Chem*. 273 (52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 80% identity, preferably 85%, 90%, or 95% identity over a specified region such as the hElk P-S6 region or the extended P-S6 region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math*. 2:482 (1981), by the homology alignment algorithm of Needleman & Wunsch, *J. Mol. Biol*. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol*. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res*. 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992));

An "anti-hElk" antibody is an antibody or antibody fragment that specifically binds a polypeptide encoded by the hElk gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to hElk, encoded in SEQ ID NO:1, splice variants, or portions thereof, can be selected to obtain only those polyclonal antibodies that are specifically immunoreactive with hElk and not with other proteins, except for polymorphic variants, orthologs, and alleles of hElk. This selection may be achieved by subtracting out antibodies that cross-react with molecules such as *Drosophila* Elk and other Elk orthologs, and with other family members such as rat and mouse Eag. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains hElk or nucleic acid encoding hElk protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating the Gene Encoding hELK

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts*. 22:1859-1862 (1981), using an automated synthesizer, as described in Van Devanter et.

al., *Nucleic Acids Res*. 12:6159-6168 (1984). Purification of oligonucleotides is by either native acrylamide gel electrophoresis or by anion-exchange HPLC as described in Pearson & Reanier, *J. Chrom*. 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding hElk

In general, the nucleic acid sequences encoding hElk and related nucleic acid sequence homologs are cloned from cDNA and genomic DNA libraries or isolated using amplification techniques with oligonucleotide primers. For example, hElk sequences are typically isolated from human nucleic acid (genomic or cDNA) libraries by hybridizing with a nucleic acid probe or polynucleotide, the sequence of which can be derived from SEQ ID NO:2, preferably from the region encoding the P-S6 region or from the region encoding the extended P-S6 region. A suitable tissue from which Elk RNA and cDNA can be isolated is brain tissue such as whole brain or hippocampus (see, e.g., FIG. 2).

Amplification techniques using primers can also be used to amplify and isolate hElk from DNA or RNA. The following primers can also be used to amplify a sequence of hElk: ATGCCGGCCATGCGGGGCCTCCT (SEQ ID NO:3), AGATGGCAGCACACCTGGCAACGCTG (SEQ ID NO:4) and GCCCATCTGCTGAAGACGGTGCGC (SEQ ID NO:5), CGAAGCCCACGCTGGTGAGGCTGCTG (SEQ ID NO:6). These primers can be used, e.g., to amplify either the full length sequence or a probe of one to several hundred nucleotides, which is then used to screen a human library for full-length hElk.

Nucleic acids encoding hElk can also be isolated from expression libraries using antibodies as probes. Such polyclonal or monoclonal antibodies can be raised using the sequence of SEQ ID NO:1.

Human Elk polymorphic variants, orthologs, and alleles that are substantially identical to the P-S6 region or the extended P-S6 region of hElk can be isolated using hElk nucleic acid probes and oligonucleotides under stringent hybridization conditions, by screening libraries. Alternatively, expression libraries can be used to clone hElk and hElk polymorphic variants, orthologs, and alleles by detecting expressed homologs immunologically with antisera or purified antibodies made against hElk or portions thereof (e.g., the P-S6 region or the extended P-S6 region of hElk), which also recognize and selectively bind to the hElk homolog.

To make a cDNA library, one should choose a source that is rich in hElk mRNA, e.g., tissue such as whole brain or hippocampus (see, e.g., FIG. 2). The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating hElk nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of hElk directly from mRNA, from cDNA, from genomic libraries or cDNA libraries. Degenerate oligonucleotides can be designed to amplify hElk homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of hElk encoding mRNA in physiological samples, for nucleic acid sequencing, or for other purposes. Genes amplified by the PCR reaction can be purified from agarose gels and cloned into an appropriate vector.

Gene expression of hElk can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology and the like.

Synthetic oligonucleotides can be used to construct recombinant hElk genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the hElk gene. The specific subsequence is then ligated into an expression vector.

The gene for hElk is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding hElk, one typically subclones hElk into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al, supra. Bacterial expression systems for expressing the hElk protein are available in, e.g., *E. coli, Bacillus* sp., and *Salmonella* (Palva et al. *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the hElk encoding nucleic acid in host cells. A typical expression cassette thus contains a promoter operably linked to the nucleic acid sequence encoding hElk and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to tansport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, bactilovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a hElk encoding sequence under the direction of the polyhedrin promoter or other strong baculovirus promoters.

The elements that are typically-included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of hElk protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing hElk.

After the expression vector is introduced into the cells, the transfected cells are cultured under conditions favoring expression of hElk, which is recovered from the culture using standard techniques identified below.

IV. Purification of hELK Polypeptides

Either naturally occurring or recombinant hElk can be purified for use in functional assays. Naturally occurring hElk monomers can be purified, e.g., from human tissue such as whole brain or hippocampus, and any other source of a hElk homolog. Recombinant hElk monomers can be purified from any suitable expression system.

The hElk monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant hElk monomers are being purified. For example, proteins having established molecular adhesion properties can be reversible fused to the hElk monomers. With the appropriate ligand, the hElk monomers can be selectively adsorbed to a purification column and then freed from the column in a relatively pure form. The fused protein is then removed by enzymatic activity. Finally the hElk monomers could be purified using immunoaffinity columns.

A. Purification of hElk Monomers from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the hElk monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human Elk monomers are separated from other bacterial proteins by standard separation techniques, e.g., with Ni—NTA agarose resin.

Alternatively, it is possible to purify the hElk monomers from bacteria periplasm. After lysis of the bacteria, when the hElk monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying the hELK Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the hElk monomers can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The hElk monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of hELK

In addition to the detection of hElk genes and gene expression using nucleic acid hybridization technology, one can also use immunoassays to detect the hElk monomers. Immunoassays can be used to qualitatively or quantitatively analyze the hElk monomers. A general overview of the applicable technology can be found in Harlow & Lane, *Antibodies: A Laboratory Manual* (1988).

A. Antibodies to hElk Monomers

Methods of producing polyclonal and monoclonal antibodies that react specifically with the hElk monomers are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of hElk monomers may be used to produce antibodies specifically reactive with hElk monomers. For example, recombinant hElk monomers or an antigenic fragment thereof, such as the P-S6 region or the extended P-S6 region, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-hElk proteins, other Elk orthologs, other Eag family members, or other Kv superfamily members, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better.

Once the specific antibodies against a hElk are available, the hElk can be detected by a variety of immunoassay methods. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The hElk can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., $7^{th}$ ed. 1991). Immunological binding assays (or immunoassays) typically use an antibody that specifically binds to a protein or antigen of choice (in this case the hElk or an antigenic subsequence thereof). The antibody (e.g., anti-hElk) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled hElk polypeptide or a labeled anti-hElk antibody. Alternatively, the labeling agent may be a third moiety, such a secondary antibody, which specifically binds to the antibody/hElk complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting the hElk in samples may be either competitive or noncompetitive. Noncompetitive immunoassays are assays in which the amount of antigen is directly measured. In one preferred "sandwich" assay, for example, the anti-hElk subunit antibodies can be bound directly to a solid substrate on which they are immobilized. These immobilized antibodies then capture hElk present in the test sample. The hElk monomers are thus immobilized and then bound by a labeling agent, such as a second hElk antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the hElk present in the sample is measured indirectly by measuring the amount of known, added (exogenous) hElk displaced (competed away) from an anti-hElk antibody by the unknown hElk present in a sample. In one competitive assay, a known amount of the hElk is added to a sample and the sample is then contacted with an antibody that specifically binds to the hElk. The amount of exogenous hElk bound to the antibody is inversely proportional to the concentration of the hElk present in the sample. In a particularly preferred embodiment, the antibody is immobilized on a solid substrate. The amount of hElk bound to the antibody may be determined either by measuring the amount of hElk present in a hElk/antibody complex, or alternatively by measuring the amount of remaining uncomplexed protein. The amount of hElk may be detected by providing a labeled hElk molecule.

A hapten inhibition assay is another preferred competitive assay. In this assay the known hElk is immobilized on a solid substrate. A known amount of anti-hElk antibody is added to the sample, and the sample is then contacted with the immobilized hElk. The amount of anti-hElk antibody bound to the known immobilized hElk is inversely proportional to the amount of hElk present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations for hElk. For example, a protein at least partially encoded by SEQ ID NO:2 or an immunogenic region thereof, such as the P-S6 region (amino acids 452-514), or an immunogenic region thereof, such as the extended P-S6 region (amino acids 452-710), can be immobilized to a solid support. Other proteins such as other Elk subfamily members, e.g., *Drosophila* Elk, are added to the assay so as to compete for binding of the antisera to the immobilized antigen. The ability of the added proteins to compete for binding of the antisera to the immobilized protein is compared to the ability of the hElk encoded by SEQ ID NO:1 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele, ortholog, or polymorphic variant of hElk, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by hElk that is required to inhibit 50% of binding, then the second protein is said to specifically bind to the polyclonal antibodies generated to the respective hElk immunogen.

Other Assay Formats

Western blot (immunoblot) analysis is used to detect and quantify the presence of the hElk in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind hElk. The anti-hElk antibodies specifically bind to hElk on the solid support. These antibodies may be directly labeled or alternatively may be subsequently detected using labeled antibodies (e.g., labeled sheep anti-mouse antibodies) that specifically bind to the anti-hElk antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize hElk, or secondary antibodies that recognize anti-hElk antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of hELK

A. Assays

Human Elk monomers and hElk alleles, orthologs, and polymorphic variants are subunits of voltage-gated potassium channels. The activity of a potassium channel comprising hElk can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising hElk. Such modulators of a potassium channel are useful for treating various disorders involving potassium channels. Treatment of dysfunctions include, e.g., endocrine disorders, CNS disorders such as migraines, hearing and vision problems, psychotic disorders, seizures, and use as neuroprotective agents (e.g., to prevent stroke). Such modulators are also useful for investigation of the channel diversity provided by hElk and the regulation/modulation of potassium channel activity provided by hElk.

Modulators of the potassium channels are tested using biologically active hElk, either recombinant or naturally occurring. Human Elk can be isolated, co-expressed or expressed in a cell, or expressed in a membrane derived from a cell. In such assays, hElk is expressed alone to form a homomeric potassium channel or is co-expressed with a second alpha subunit (e.g., another Kv superfamily member or an Eag family member, preferably an Elk subfamily member) so as to form a heteromeric potassium channel. Elk can also be expressed with additional beta subunits. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising hElk is achieved when the potassium channel activity value relative to the control is about 90%, preferably 50%, more preferably 25%. Activation of channels comprising hElk is achieved when the potassium channel activity value relative to the control is 110%, more preferably 150%, more preferable 200% higher. Compounds that increase the flux of ions will cause a detectable increase in the ion current density by increasing the probability of a channel comprising hElk being open, by decreasing the probability of it being closed, by increasing conductance through the channel, and/or by allowing the passage of ions.

Changes in ion flux may be assessed by determining changes in polarization (i.e., electrical potential) of the cell or membrane expressing the potassium channel comprising hElk. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575-1595 (1997)).

Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Holevinsky et al., *J. Membrane Biology* 137:59-70 (1994)). Assays for compounds capable of inhibiting or increasing potassium flux through the channel proteins comprising hElk can be performed by application of the compounds to a bath solution in contact with and comprising cells having a channel of the present invention (see, e.g., Blatz et al., *Nature* 323:718-720 (1986); Park, *J. Physiol.* 481:555-570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

Preferably, the Elk that is a part of the potassium channel used in the assay will have the sequence displayed in SEQ ID NO:1 or a conservatively modified variant thereof. Alternatively, the Elk of the assay will be derived from a eukaryote and include an amino acid subsequence having substantial amino acid sequence identity to the P-S6 region or the extended P-S6 region of hElk. Generally, the amino acid sequence identity will be at least 80%, preferably at least 85 to 90%, most preferably at least 95%.

Human Elk orthologs will generally confer substantially similar properties on a channel comprising such hElk, as described above. In a preferred embodiment, the cell placed in contact with a compound that is suspected to be a hElk homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to hElk are considered homologs or orthologs of hElk.

B. Modulators

The compounds tested as modulators of Elk channels comprising a human Elk subunit can be any small chemical compound, or a biological entity, such as a protein, sugar, nucleic acid or lipid. Alternatively, modulators can be genetically altered versions of a human Elk subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci.* USA 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g. U.S. Pat. No. 5,539,083), antibody libraries (see, e.g., Vaughn et al., *Nature Biotechnology*, 14 (3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a Elk channel comprising a human Elk subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 about 1500 different compounds. It is possible to assay several different plates per day; assay screens for up to about 6,000-20,000 different compounds is possible using the integrated systems of the invention.

VII. Computer Assisted Drug Design Using hELK

Yet another assay for compounds that modulate the activities of hElk involves computer assisted drug design, in which a computer system is used to generate a three-dimensional structure of hElk based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where hElk interacts with other potassium channel subunits.

The three-dimensional structural model of the protein is generated by entering channel protein amino acid sequences of at least 25, 50, 75 or 100 amino acid residues or corresponding nucleic acid sequences encoding an hElk monomer into the computer system. The amino acid sequence of each of the monomers is selected from the group consisting of SEQ ID NO:1 and a conservatively modified versions thereof. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of hElk protein to identify ligands that bind to hElk. Binding affinity between the protein and ligands is determined using energy terms to determine which ligands have an enhanced probability of binding to the protein.

Computer systems are also used to screen for mutations, polymorphic variants, alleles and interspecies homologs of hElk genes. Such mutations can be associated with disease states. Once the variants are identified, diagnostic assays can be used to identify patients having such mutated genes associated with disease states. Identification of the mutated hElk genes involves receiving input of a first nucleic acid, e.g., SEQ ID NO:2, or an amino acid sequence encoding hElk, selected from the group consisting of SEQ ID NO:1, and a conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in hElk genes, and mutations associated with disease states. The first and second sequences described above can be saved on a computer readable substrate.

Human Elk monomers and the potassium channels containing these hElk monomers can be used with high density oligonucleotide array technology (e.g., GeneChip™) to identify homologs and polymorphic variants of hElk in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

VIII. Cellular Transfection and Gene Therapy

The present invention provides the nucleic acids of hElk for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for hElk, under the control of a promoter, then expresses a hElk monomer of the present invention, thereby mitigating the effects of absent, partial inactivation, or abnormal expression of the hElk gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6 (10):1149-1154 (1998); Vigne, *Restorative Neurology and Neuroscience* 8:35-36 (1995); Kremer & Perricaudet, *British Medical Bulletin* 51 (1):31-44 (1995); Haddada et al., in *Current Topics in Microbiology and Immunology* (Doerfler & Böhm eds., 1995); and Yu et al., *Gene Therapy* 1:13-26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995);

Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adenoassociated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *Proc. Natl. Acad. Sci. U.S.A.* 81:6466-6470 (1984); and Samulski et al., *J. Virol.* 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc. Natl. Acad. Sci. U.S.A.* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors (Ellem et al., *Immunol Immunother.* 44 (1):10-20 (1997); Dranoff et al., *Hum. Gene Ther.* 1:111-2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702-3 (1998), Kearns et al., *Gene Ther.* 9:748-55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 241:5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panb cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the Elk channels comprising a human Elk alpha subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Transduced cells are prepared for reinfusion according to established methods (see, e.g., Abrahainsen et al., *J. Clin. Apheresis* 6:48—53 (1991); Carter et al., *J. Clin. Apheresis* 4:113-117 (1998); Aebersold et al., *J. Immunol. Meth.* 112: 1-7 (1998); Muul et al., *J. Immunol. Methods* 101:171-181 (1987); and Carter et al., *Transfusion* 27:362-365 (1987)).

X. Kits

Human Elk and its homologs are useful tools for examining expression and regulation of potassium channels. Human Elk-specific reagents that specifically hybridize to hElk nucleic acid, such as hElk probes and primers, and hElk-specific reagents that specifically bind to the hElk protein, e.g., hElk antibodies are used to examine expression and regulation.

Nucleic acid assays for the presence of hElk DNA and RNA in a sample include numerous techniques are known to those skilled in the art, such as Southern analysis, northern analysis, dot blots, RNase protection, S1 analysis, amplification techniques such as PCR and LCR, and in situ hybridization. In situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, hElk protein can be detected with the various immunoassay techniques described above. The test sample is typically compared to both a positive control (e.g., a sample expressing recombinant hElk monomers) and a negative control.

The present invention also provides for kits for screening modulators of the heteromeric potassium channels. Such kits can be prepared from readily available materials and reagents. For example, such kits can comprise any one or more of the following materials: hElk monomers, reaction tubes, and instructions for testing the activities of potassium channels containing hElk. A wide variety of kits and components can be prepared according to the present invention, depending upon the intended user of the kit and the particular needs of the user. For example, the kit can be tailored for in vitro or in vivo assays for measuring the activity of a potassium channel comprising a hElk monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example I

Cloning and Expression of hELK

Using PCR and primers, according to standard conditions, hElk is amplified from brain tissue cDNA, e.g., whole brain or hippocampus cDNA. The following primers were used for amplification: ATGCCGGCCATGCGGGGCCTCCT (SEQ ID NO:3), AGATGGCAGCACACCTG-GCAACGCTG (SEQ ID NO:4).

The cDNA is prepared from total RNA isolated from brain tissue, e.g., whole brain or hippocampus, according to standard methods. hElk is amplified with the primers described above using the following conditions: 15 seconds at 96° C., 15 seconds at 72-60° C., and 3 minutes at 72° C. for 40 cycles.

The PCR products are subcloned into plasmids and sequenced according to standard techniques. The nucleotide and amino acid sequences of hElk are provided, respectively, in SEQ ID NO:2 and SEQ ID NO:1 (see FIG. 1 for an amino acid alignment of human and *Drosophila* Elk).

mRNA distribution of hElk was examined according to standard techniques (see FIG. 2).

Example II

Figure 3A:
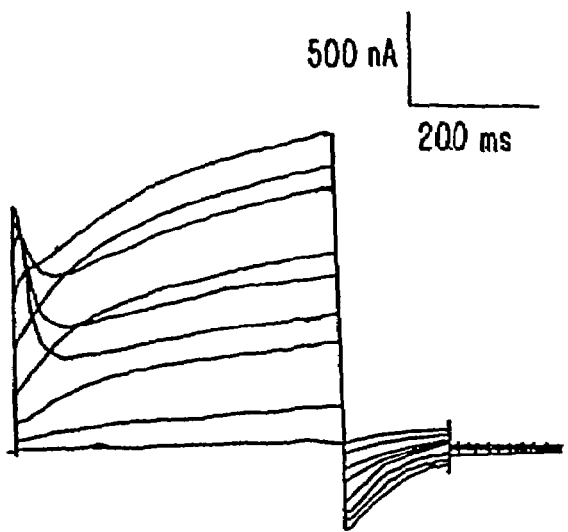
FIG. 3. Expression of hElk in *Xenopus* oocytes. (A) hElk currents elicited in response to 480 ms depolarizations from −80 mV to +80 mV in 20 mV increments. The holding potential was −90 mV and the tail currents were measured at −120 mV. Note that there is substantial inactivation at higher voltages. (B) Plot of tail current amplitude vs. holding potential for the traces shown in (A). A single boltzman fit of the data yields a half-activation voltage of −34 mV. (C) Blockade of hElk by 3 mM barium. Currents were elicited by 480 ms depolarizations to +20 mV from a holding potential of −90 mV, with tail currents measured at −120 mV. Traces show control current, block by barium, and reversal of block following washout of barium.
Figure 3B:
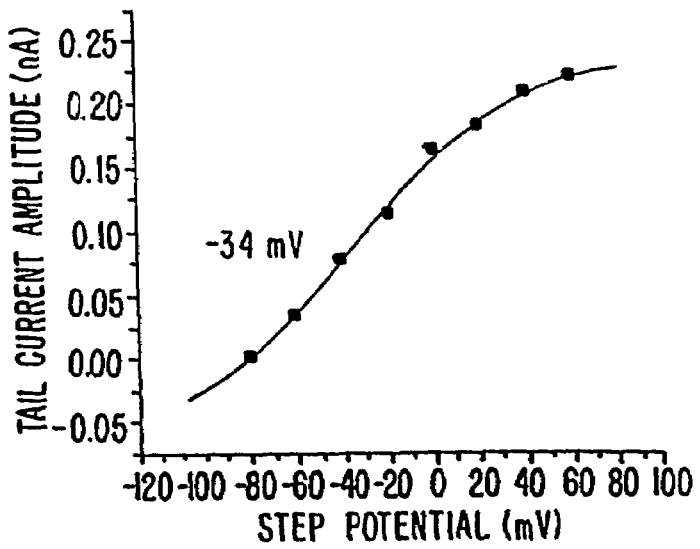
Figure 3C:
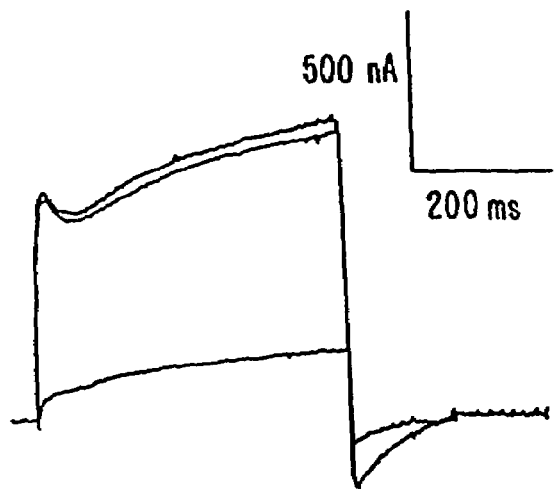
Figure 4A:
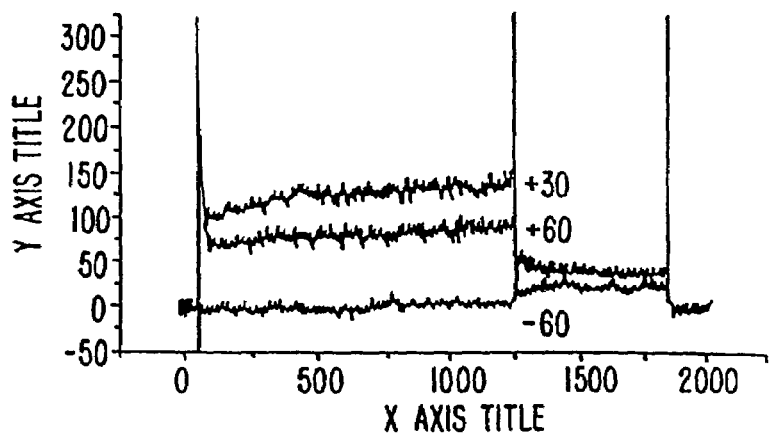
FIG. 4. Expression of hElk in Chinese Hamster Ovary Cells. (A) Currents elicited from a CHO cell expressing hElk in response to depolarization to −60, +30, and +60 mV from a holding potential of −80 mV. Tail currents were measured at −40 mV. Note the fast-inactivating component seen at +30 mV and +60 mV. (B) Current/voltage relationship for a CHO cell expressing Elk. There is a substantial reduction in hElk current at high voltages due to inactivation. (C) Reactivation of hElk after recovery from inactivation. A four second pulse to +40 mV was used to activate hElk. This pulse was followed by a 12.5 ms repolarization to −90 mV to allow for recovery from inactivation and a second depolarizing pulse to reactivate hElk ranging from −2-mV to +90 mV in 10 mV increments.
Figure 4B:
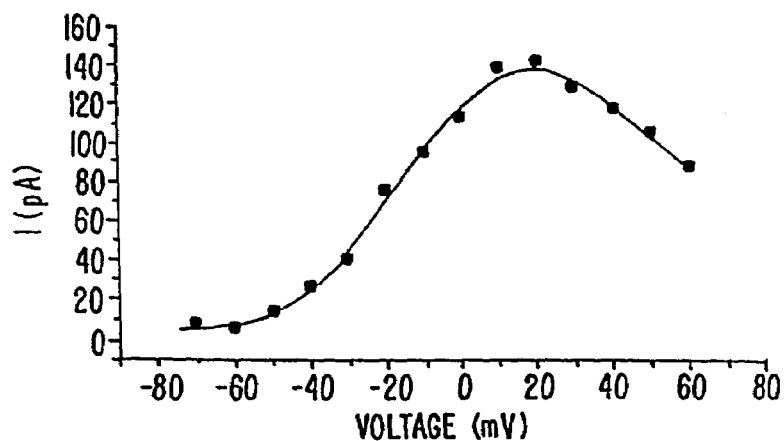
Figure 4C:
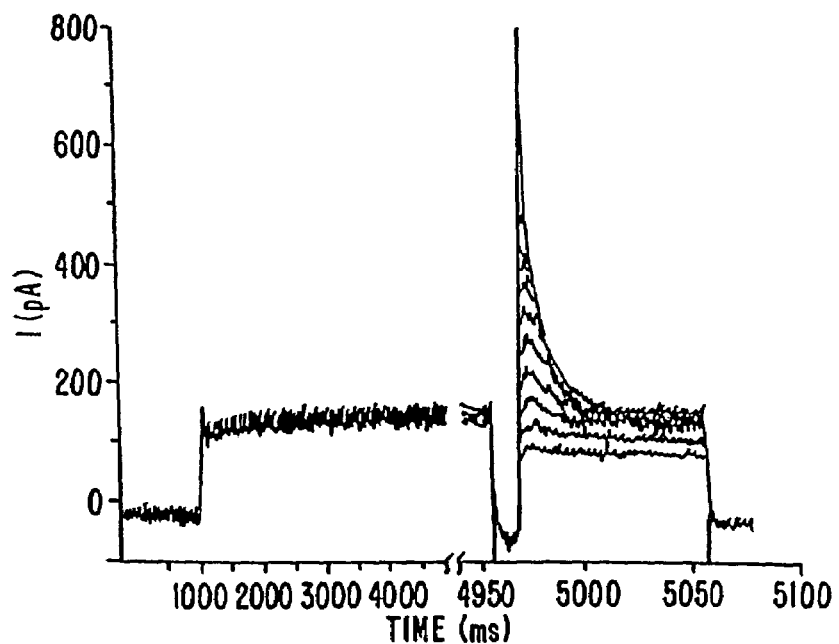

Expression and Voltage-Gated Activity of Homomeric Channels Containing hElk Monomers hElk monomer was expressed in both *Xenopus* oocytes and CHO cells according to standard methodology, to demonstrate its ability to form homomeric potassium channels with voltage-gated activity (see FIGS. 3 and 4). Changes in current magnitude can be indirectly measured using a reporter voltage-sensitive fluorescent dye (see, e.g., Etts et al., *Chemistry and Physiology of Lipids*, 69:137 (1994)). Changes in current magnitude can also be measured directly using electrophysiology, and by measuring ion flux.

hElk channels are potassium selective and voltage-gated. These channels open in a time-dependent manner in response to depolarization, and have a significant probability of opening at voltages more positive than about −70 mV. There is substantial reduction in hElk current at high voltages due to inactivation (see FIG. 4).

Example III

Genomic Localization of the hElk Gene

Genomic localization for the hElk gene was determine by amplifying the Stanford Genome Center's G3 Radiation Hybrid panel with the following hElk specific oligonucleotides:

```
CACCTGGGATGGCTTCATCCTGCTC     (SEQ ID NO:7)

AAACACCACCTGGCCCGACTTGGAC     (SEQ ID NO:8)
``` hElk was found to be linked to marker SHCG-33198 with an LOD score of 6.075282, placing the hElk gene approximately 100 kbp from this marker (e.g., 4.71 millirads). This marker is on chromosome 12 and appears to be in the 12pter-12qter band near 12q13. The Gene Location database maps a nearby marker (SHGC-30065) at 52.32 centimorgans from the top of the chromosome 12 recombination group. The closest mapping disease in this group is Allgrove syndrome, which is a rare adrenal insufficiency associated with a collection of poorly defined neuropathies. Although Allgrove appears to fall between markers that may exclude hElk, it is possible that hElk maps to Allgrove.

The invention claimed is:

1. An antibody that selectively binds to a polypeptide consisting of the amino acid sequence of SEQ ID NO:1, wherein the selective binding is at least twice background signal.

2. The antibody of claim 1, which is a polyclonal antibody.

3. The antibody of claim 1, which is a monoclonal antibody.

* * * * *